United States Patent
Zofchak et al.

(10) Patent No.: US 7,101,954 B2
(45) Date of Patent: *Sep. 5, 2006

(54) POLYMERIC URETHANE ESTER QUATS AND THEIR USE IN PERSONAL CARE COMPOSITIONS

(75) Inventors: Albert A. Zofchak, Holmdel, NJ (US); John Obeji, Clifton, NJ (US)

(73) Assignee: Alzo International, Inc., Sayreville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/484,401

(22) PCT Filed: Aug. 14, 2002

(86) PCT No.: PCT/US02/25775

§ 371 (c)(1),
(2), (4) Date: Jun. 18, 2004

(87) PCT Pub. No.: WO03/016247

PCT Pub. Date: Feb. 27, 2003

(65) Prior Publication Data

US 2004/0234562 A1 Nov. 25, 2004

Related U.S. Application Data

(63) Continuation-in-part of application No. 09/933,108, filed on Aug. 20, 2001, now Pat. No. 6,800,716.

(51) Int. Cl.
*C08G 18/36* (2006.01)
(52) U.S. Cl. .................. 528/74.5; 528/71; 554/106; 560/26; 560/115; 560/158; 424/70.11; 424/70.28; 424/78.03; 424/78.17; 424/401

(58) Field of Classification Search ............... 528/74.5, 528/71; 554/106; 560/26, 115, 158; 424/70.11, 424/70.28, 78.03, 78.17, 401
See application file for complete search history.

(56) References Cited

U.S. PATENT DOCUMENTS

| 4,581,387 A | 4/1986 | Werner |
| 5,157,056 A | 10/1992 | McGovern |
| 5,926,901 A | 7/1999 | Tseng et al. |
| 6,800,716 B1 * | 10/2004 | Zofchak et al. ............ 528/74.5 |

FOREIGN PATENT DOCUMENTS

| EP | 0 705 871 A | 4/1996 |
| RU | 2 131 440 C | 6/1999 |
| WO | WO 95/10500 A | 4/1995 |
| WO | WO 96/33230 A | 10/1996 |

OTHER PUBLICATIONS

Database WPI, Week 198543, Derwent Publications Ltd., London, GB; AN 1985-265808; XP002324731; "Polyol composition useful as raw material for polyurethane resin"; & JP 60 177013 A(ITO SEIYU) Nov. 9, 1985 *abstract*.

* cited by examiner

*Primary Examiner*—Rachel Gorr
(74) *Attorney, Agent, or Firm*—Henry D. Coleman; Coleman Sudol Sapone, P.C.

(57) ABSTRACT

The present invention relates to a composition and use of polymeric urethane esters quats as an active ingredient for skin and hair contacting personal care compositions and products related thereto. These compositions are generally produced by the reaction of a trialkanolamine with a hydroxy fatty acid to produce a trialkanolamine fatty acid ester, which is then polymerized with a diisocyanate and in preferred embodiments, further reacted with a quaternizing agent to produce preferred quaternized compositions according to the present invention.

31 Claims, 3 Drawing Sheets

TEA RICINOLEATE

POLYDERM PPI-TEA DIRICINOLEATE / IPDI COPOLYMER

Step # 2

DERMOQUAT TEA DIRICINOLEATE / IPDI COPOLYMER / DES

Step # 3

POLYMERIC URETHANE ESTER QUATS AND THEIR USE IN PERSONAL CARE COMPOSITIONS

RELATED APPLICATIONS

This application is a §371 filing of PCT/US/02/25775, filed Aug. 14, 2002, and a continuation-in-part application of Ser. No. 09/933,108, now U.S. Pat. No. 6,800,716.

FIELD OF THE INVENTION

This invention relates to novel Polymeric Urethane compositions which are obtained by reacting trialkanolamines with hydroxy fatty acids to form mono, di and/or triesters, which are further reacted with diisocyanates to form polymers, which are thereafter quaternized. The resultant polymeric urethane ester quaternary compositions of the present invention exhibit the normal characteristics of existing quaternary compositions such as conditioning, prevention of static charge and softening, emolliency, lubricity, enhanced wet and dry compability, and in addition, increased adhesion to the skin and hair. Also, increased adhesion to the skin and hair occurs as a result of the presence of the urethane linkages directly attributable to the diurethane functionalities which enhance the cationic character of tenacity of the present invention in skin and hair contacting formulations.

BACKGROUND OF THE INVENTION

Quaternary amine-containing compositions have long been in existence and have been used in a myriad of applications. These compositions range from derivatives of tallow such as Dimethyl Di-Hydrogenated Tallow Ammonium Chloride which has been the standard for fabric softeners and as an antistat in fabric spray applications. Quaternaries based on Benzyl Chloride, i.e., Benzylkonium Chloride have been used in conditoners for hair; but the tendency has been to shy away from the Benzene radical, which has some definite irritation and toxicological properties. Quaternaries such as Trimethyl Cetyl ammonium chloride has long been used in hair conditioners for their outstanding compability and antistatic properties. The drawback of the prior art composition is the viscosity which necessitates the addition of water and/or solvents to make the product useable by the cosmetic manufacturer.

In contrast to the art, the compositions according to the present invention bring novel unanticipated properties which can be traced to the presence of the "urethane linkage" within the polymer. This linkage synergistically increased adhesion to hair and skin contacting formulations resulting in the use of less quaternary than those products which are available in the current marketplace, thus resulting in a significant reduction in the cost of manufacturing personal care products. In addition, the use of polyurethane allows the manufacturer a considerable degree of flexibility for formulation due to the viscosity and molecular weight of the composition, which may vary as a function of the polymeric chain size and substituents.

BRIEF DESCRIPTION OF THE INVENTION

One aspect of the present invention relates to a polymeric urethane ester quaternary composition which is made by reacting a trialkanolamine with a hydroxy-containing fatty acid to form a mono-, di- or triester. The ester obtained is then reacted with a diisocyanate as otherwise described herein to produce a polyurethane ester containing tertiary amine groups which tertiary amine groups may be quaternized with a quaternizing agent in optional preferred embodiments according to the present invention. Methods of making and using these compositions are also contemplated by the present invention as are personal care products which include these compositions.

Preferred non-quaternized compositions according to the present invention may be represented by a chemical formula represented by Formula I:

Formula I

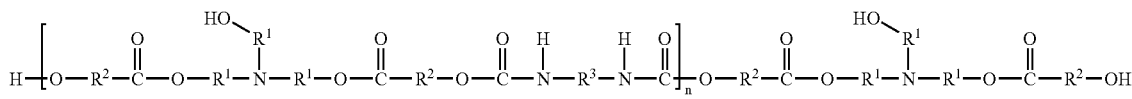

wherein $R^1$ is a $C_2$ to $C_{12}$ saturated or unsaturated, linear, branch-chained, cyclic or aromatic hydrocarbon group which is either unsubstituted or substituted with a pendant hydroxyl group, but is preferably unsubstituted;

$R^2$ is a $C_1$ to $C_{24}$ saturated or unsaturated, linear, branch-chained, cyclic or aromatic hydrocarbon group wherein said hydrocarbon group may be a phenyl or benzyl group or substituted phenyl or benzyl group, an alkylphenyl, alkylbenzyl or a substituted alkylphenyl or alkylbenzyl group; and $R^3$ is a $C_2$ through $C_{22}$ (preferably, $C_6$ through $C_{12}$) linear, cyclic or branch-chained saturated or unsaturated hydrocarbon group which is substituted or unsubstituted, an aromatic group, including a phenyl or benzyl group or substituted phenyl or benzyl group, an alkylphenyl, alkylbenzyl or substituted alkylphenyl or alkylbenzyl group; and n is an integer from about 2 to 5,000, preferably about 2 to 1000, more preferably about 10 to 500.

Preferred quaternized compositions according to the present invention may be represented by a chemical formula represented by formula II:

Formula II

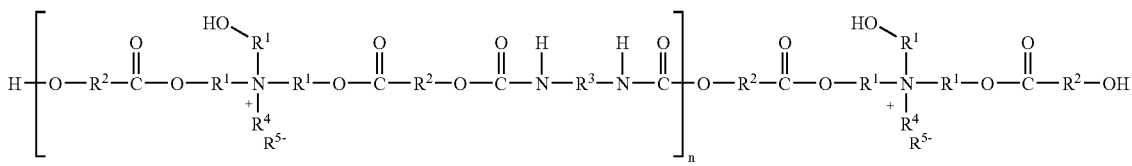

wherein $R^1$ is a $C_2$ to $C_{12}$ saturated or unsaturated, linear, branch-chained, cyclic or aromatic hydrocarbon group which is either unsubstituted or substituted with a pendant hydroxyl group, but is preferably unsubstituted;

$R^2$ is a $C_1$ to $C_{24}$ saturated or unsaturated, linear, branch-chained, cyclic or aromatic hydrocarbon group wherein said hydrocarbon group may be a phenyl or benzyl group or substituted phenyl or benzyl group, an alkylphenyl, alkylbenzyl or a substituted alkylphenyl or alkylbenzyl group;

$R^3$ is a $C_2$ through $C_{22}$ (preferably, $C_6$ through $C_{12}$) linear, cyclic or branch-chained saturated or unsaturated hydrocarbon group which is substituted or unsubstituted, an aromatic group, including a phenyl or benzyl group or substituted phenyl or benzyl group, an alkylphenyl, alkylbenzyl or substituted alkylphenyl or alkylbenzyl group;

$R^4$ is an electron pair (unsubstituted) or a quaternizing group;

$R^5$ is non-existent (unreacted) or is a counterion to the quaternizing group; and n is an integer from about 2 to 5,000, preferably about 2 to 1000, more preferably about 10 to 500.

In preferred aspects of the present invention, $R^3$ is a $C_{10}$ hydrocarbon, more preferably a methyl substituted cyclohexyl or isophorone group which is obtained after reaction of isophorone diisocyanate with the trialkanolamine esters. Preferably, $R^2$ is obtained from the reaction of a fatty acid selected from the group consisting of caproic, caprylic, capric, lauric, myristic, palmitic, stearic, arachadonic acid, linoleic, oleic, linoleic, linolenic, 2-ethylhexoic, isooctanoic, pelargonic, heptanoic, undecanoic, isolauric, isomyristic, isopalmitic, isostearic and mixtures such as those generally known in the art as coconut fatty acids, palm kernal fatty acids, soybean fatty acids, safflower fatty acids, castor oil, etc. In addition to the aforementioned acids, alpha hydroxy acids such as lactic acid, glycolic acid, invention include for example, lactic acid, glycolic acid, alpha hydroxy butyric acid, alpha hydroxy pentanoic acid, alpha hydroxy hexanoic acid, alpha hydroxy heptanoic acid, alpha hydroxy octanoic acid, alpha hydroxy nonanoic acid, alpha hydroxy decanoic acid, alpha hydroxy dodecanoic acid, among others and beta-hydroxy acids such as salicylic acid, among numerous others, as well a ricinoleic and 12-hydroxystearic cid. In more preferred aspects of the present invention, the fatty acid is selected from the group consisting of ricinoleic acid, 12-hydroxystearic acid or mixtures thereof, or representative mixtures of fatty acids obtained from sources (triglycerides) such as castor oil, coconut oil, palm kernel oil, soybean oil, safflower oil, rape seed (canola) oil, among others. Preferred alpha hydroxy acids include lactic acid and glycolic acid. Noted here is the fact that in certain transesterification reactions involving trialkanolamines and triglycerides, the trialkanol fatty ester may represent a mixture of compositions having various fatty acid group substituents.

In particularly preferred aspects of the present invention, the trialkanolamine is triethanolamine, the acid is ricinoleic acid, lactic acid or salicylic acid, or a mixture of any one or more of the aforementioned acids in combination with erucic acid and/or oleic acid. Mixtures of lactic acid and erucic acid or salicylic acid and oleic acid are also preferred for use in the present invention.

The present invention relates to polymeric urethane ester quaternary compositions ("polymeric urethane ester quats") which are produced by taking trialkanolamines and reacting the alkanol groups with fatty acids to produce amine mono- di and triester, preferably di-esters, subjecting the di-esters to chain extension polymerization with a diisocyanate and then quaternizing free tertiary amine groups to produce compositions according to the present invention. The fatty acids which are used may be linear, isomeric or aromatic in structure ranging in length from $C_2$ to $C_{22}$ carbon atoms and in addition to containing a carboxylic acid group, also contain at least one free hydroxyl group. Included within this range of fatty acids are derivatives of Castor Oil such as 12-hydroxystearic acid, ricinoleic acid as well as castor itself.

Methods of using the present compositions in personal care products and methods of making personal care products are also aspects of the present invention.

The present compositions, when formulated in personal care products, including shampoos and conditioning products, instill exceptional characteristics of surfactancy, sheen, wet-comb, dry-comb, anti-static properties and conditioning qualities to the personal care products.

BRIEF DESCRIPTION OF THE FIGURES

Attached In FIG. 1, step 1, trialkanolamine fatty acid ester is produced. In FIG. 2, step 2, the trialkanolamine fatty acid ester is polymerized with diisocyante and in FIG. 3, step 3, the polymerized trialkanolamine fatty acid ester is quaternized to produced certain preferred compositions according to the present invention.

DETAILED DESCRIPTION OF THE INVENTION

Figure 1:
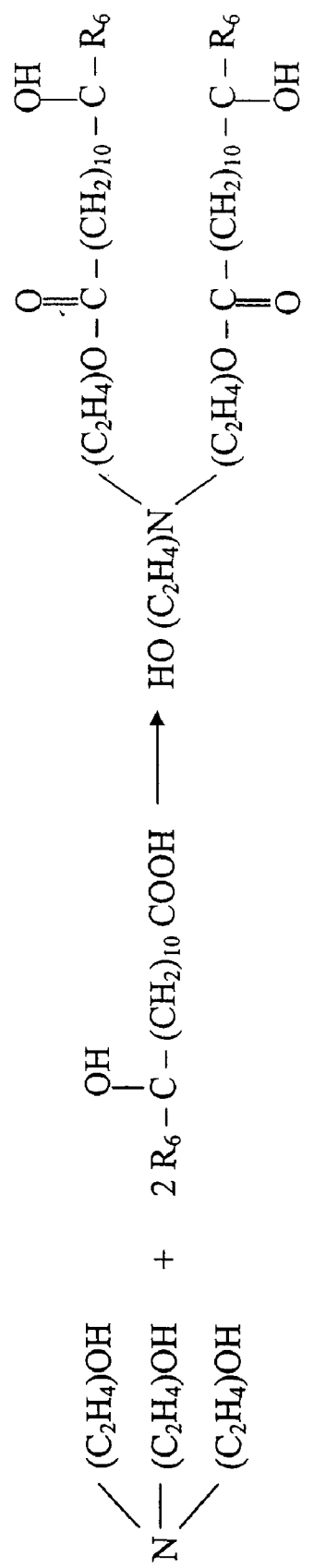
FIGS. 1–3 are representative of the series of reaction steps which produce the present compositions.
Figure 2:
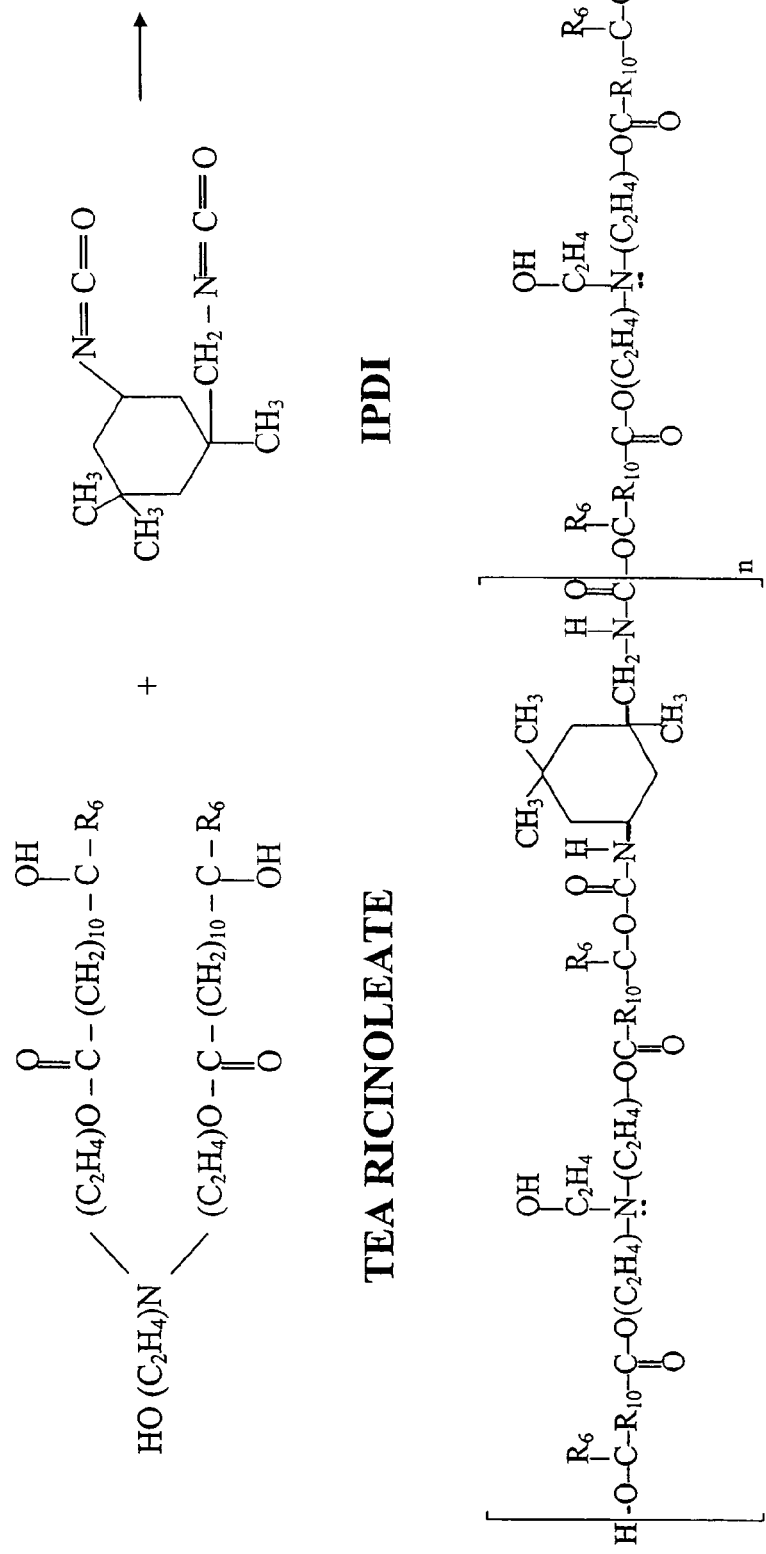
Figure 3:
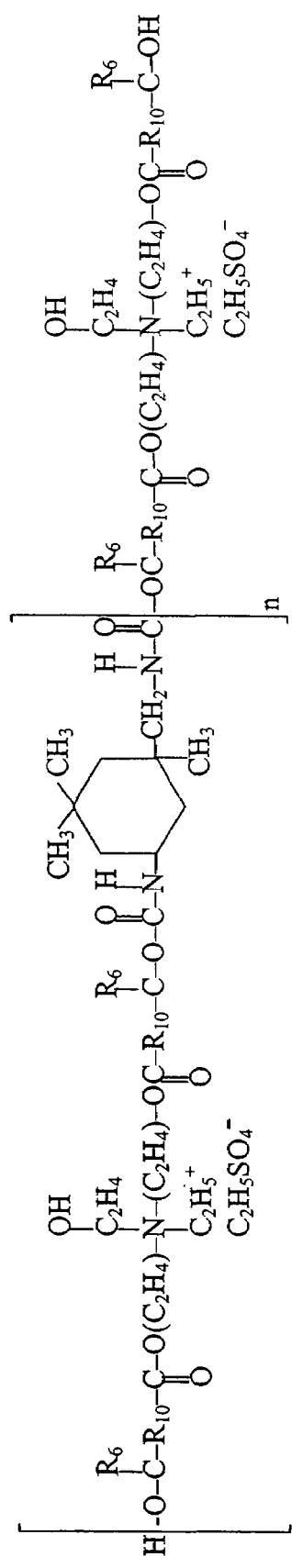

The following definitions shall be used throughout the specification to describe the present invention.

The term "personal care product" is used throughout the specification to describe a cosmetic and/or toiletry product which is preferably used on or in contact with the hair, skin and/or nails and which include effective concentrations of one or more of the compositions according to the present invention. Personal care products include, for example, cosmetics, floating bath oils, after shaves, creams, lotions, deodorants, including stick deodorants, pre-electric shave lotions, after-shave lotions, antiperspirants, shampoos, hair-coloring products, conditioners, rinses and related products, among others, including skin care products, eye makeups, body shampoos, protective skin formulations, lipsticks, lip glosses, after-bath splashes, presun and sun products, including sunscreens. Virtually any chemical product which comes into contact with the hair or skin and which may include effective amounts or concentrations of one or more of the compositions according to the present invention may be considered a personal care product according to the present invention. Preferred personal care products include conditioning agents and shampoos.

The term "effective" is used to describe amounts of compositions, components, solvents, other materials or conditions (including temperature) which are used in the present invention to produce an intended result. For example, compositions according to the present invention are added or included in personal care formulations or compositions in amounts which produce the result intended by the inclusion of the component or use of the condition.

The term "hydrocarbon" is used throughout the specification to describe various substituent groups according to the present invention. The term hydrocarbon embraces, but is not limited to, for example, alkyl, alkene groups (including those groups containing more than one unsaturated double bond), alkyne groups, aryl groups, aralkyl groups and related groups which are comprised of carbon and hydrogen atoms, such as alkylene groups (which are similar to alkyl groups except they are substituted at two carbons of the hydrocarbon with atoms or substituents other than hydrogen rather than one as is the case with alkyl groups) and related hydrocarbon radicals which may be found in the present compositions. In certain cases the term "alkyl" (or related alkyl groups such as methyl, phenyl, benzyl, etc.) is used interchangeably with a di-substituted hydrocarbon group such as an alkylene, methylene, phenylene, etc. depending upon the appearance or position of the group within the chemical structure or molecule. Hydrocarbons according to the present invention may be linear, cyclic or branch-chained, substituted (i.e., have pendant halogen, hydroxyl or other groups) or unsubstituted (i.e., comprised exclusively of C and H atoms) monomeric or dimeric (or even of higher order), aromatic, including phenyl or benzyl or substituted phenyl or benzyl group, alkylphenyl, alkylbenzyl or substituted alkylphenyl or alkylbenzy, etc.

The term "trialkanolamine" shall refer to a teriary substituted amine which has alcohol groups emanating from the amine group by way of attachment through a hydrocarbon, preferably an alkylene group. The alkylene groups may be the same or different, but are preferably the same. An example of such a component is triethanolamine. Another is tripropanolamine. $C_2$ to $C_{12}$ trialkanolamine products find use in the present invention. The trialkanolamine is substituted with at least one hydroxyl group on each alkyl group, preferably only one hydroxyl group and may be substituted with other hydroxyl groups, in addition to other cosmetically or pharmaceutically compatible groups. Other alkanolamines include, for example, diethanolmonoisopropanolamine, triisopropanolamine, triisobutanolamine, triisopentanolamine, triisohexanolamine, monoethanoldiisopropanolamine, monoethanoldiisobutanolamine, among numerous others. The trialkanolamine may be represented by the formula:

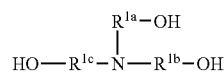

wherein each of $R^{1a}$ $R^{1b}$ and $R^{1c}$ is the same or different and is a $C_2$ to $C_{12}$ saturated or unsaturated, linear, branch-chained, cyclic or aromatic hydrocarbon group which is either unsubstituted or substituted with a pendant hydroxyl group. More preferably, the trialkanolamine is represented by the formula:

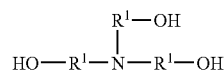

where each of $R^{1a}$ $R^{1b}$ and $R^{1c}$ above is the same and is represented more generically by $R^1$.

The term "fatty acid" is used herein to describe a $C_2$ to $C_{25}$ carboxylic acid, preferably a $C_{10}$ to $C_{22}$ fatty acid which preferably contains at least one primary, secondary, or tertiary hydroxyl group in addition to the carboxylic acid group. By using a carboxylic acid which contains at least one additional hydroxyl group in order to produce compositions according to the present invention, a trialkanolamine fatty acid ester has at least one free hydroxyl group which can further participate in a polymerization reaction, and in particular, a reaction with a diisocyanate compound to form a urethane.

The term "trialkanolamine fatty acid ester" is used to describe the reaction product of trialkanolamine and fatty acids according to the present invention to produce esters by reacting the alcohol group (i.e., primary, secondary or tertiary) of the trialkanolamine group with the hydroxy fatty acid to produce the ester, which is subsequently reacted with diisocyanate to produce a "polyurethane trialkanolamine fatty acid ester" of the present invention. Trialkanolamine fatty acids according to the present invention may be monoesters (one ester formed from reaction of a fatty acid on a single hydroxyl group in the triethanolamine molecule), diesters (two esters formed) or triesters (three esters formed). Notwithstanding the reaction of one or more of the hydroxyl groups from the triethanolamine group, the hydroxyl group from the hydroxy fatty acid will nonetheless be available for polymerization with a diisocyanate.

The term "diisocyanate" refers to a diisocyanate compound used in the present invention to react with free hydroxyl groups on the trialkanolamine fatty acid ester to form (poly)urethane compounds which may be quaternized to produce the present compositions. The term "diisocyanate" is used throughout the specification to describe a linear, cyclic or branch-chained hydrocarbon having two free isocyanate groups. $C_4$ to $C_{24}$ diisocyanate compounds are contemplated for use in the present invention, with preferred diisocyanates being $C_6$ to $C_{12}$ diisocyanates. The term "diisocyanate" also includes halogen substituted linear, cyclic or branch-chained hydrocarbons having two free isocyanate groups. Exemplary diisocyanates include, for example, isophoronediisocyanate, m-phenylene-diisocyanate, p-phenylenediisocyanate, 4,4-butyl-m-phenylene-diisocyanate, 4-methoxy-m-phenylenediisocyanate, 4-phenoxy-m-phenylenediisocyanate, 4-chloro-m-phenyldiisocyanate, toluenediisocyanate, m-xylylenediisocyanate, p-xylylenediisocyanate, 1,4-napthalenediisocyanate, cumene-1,4-diisocyanate, durene-diisocyanate, 1,5-napthylenediisocyanate, 1,8-napthylenediisocyanate, 1,5-tetrahydronapthylenediisocyanate, 2,6-napthylenediisocyanate, 1,5-tetrahydronapthylenediisocyanate; p,p-diphylenediisocyanate; 2,4-diphenylhexane-1,6-diisocyanate; methylenediisocyanate; ethylenediisocyanate; trimethylenediisocyanate, tetramethylenediisocyanate, pentamethylenediisocyanate, hexamethylenediisocyanate, nonamethylenediisocyanate, decamethylene-diisocyanate, 3-chloro-trimethylenediisocyanate and 2,3-dimethyltetramethylenediisocyanate, among numerous others. Isophorone diisocyanate is used the preferred diisocyanate used in the present invention.

The term "quaternizing agent" is used throughout the specification to describe compounds which are used to react with tertiary amines to produce quarternary salts according to the present invention. Quaternary salts are salts which are produced when a tertiary amine is reacted with a quaternizing agent to produce a quaternary amine (quaternium) which is substituted with four carbon-containing groups. The quaternary amine produced is cationic and is generally found complexed with an anionic group or "counterion", which is generally, but not always, derived from the quaternizing agent used to produce the quaternary amine. Exemplary quaternizing agents for use in the present invention include, for example, dimethyl sulfate, diethyl sulfate, methyl bromide, benzyl chloride, ethyl benzyl chloride, methyl benzyl chloride, dichloroethyl ether, epichlorohydrin, ethylene chlorohydrin, methyl chloride, pyridinium chloride and allyl chloride, among others, such that the group reactive with the amine produces an

(three R groups) group with the amine and the positively charged quaternary amine group is complexed with an anionic group or counterion, which is represented as $R^{5-}$. The quaternizing group is that group which results from quaternizing the tertiary amine with the quaternizing agent and includes, for example, methyl, ethyl, propyl, benzyl, phenyl, alkyl benzyl, allyl and numerous other groups. The counterion may be any group which is anionic and is compatible with the chemistry of the present invention and preferably is an anionic chloride, bromide, iodide, fluoride, carboxylate (from, for example the use of chloroacetic acid or sodium monochloroacetate as the quaternizing agent to provide an acetate which can provide both a quaternium group as well as the counterion) sulfate (mono- or di-anion, preferably alkyl substituted mono-anion such as methyl or ethyl sulfate, more preferably ethyl sulfate) and phosphate (mono-, di- and tri-anion, preferably tri-anion), among numerous others, with anionic chloride and sulfate (alkyl substituted mono-anion) being the preferred counterion $R^5$.

The term "surfactant" or "conditioning agent" is used synonymously throughout the specification with respect to the compositions of the present invention to describe compounds according to the present invention which contain a tertiary amine group which has been further reacted to form a quaternary amine group. Although compounds according to the present invention provide surfactant-like qualities, the compounds also possess qualities of emolliency, conditioning and sheen enhancing properties, among others. The compositions according to the present invention are particularly useful for use in shampoos and as viscosity control agents, especially given the fact that the reaction conditions in forming the final composition, in addition to the number of reactive primary, secondary and tertiary hydroxyl groups found in the trialkanolamine esters and/or the fatty acid substituent, may dramatically influence the molecular weight and crosslinking density of resulting polymers, thus influencing the viscosity and solubility characteristics of the present invention. It is noted here that in adjusting the molecular weight and crosslinking density of the present compositions, one of ordinary skill may readily accommodate various favorable characteristics, including keratinous tissue adhesion, sheen, conditioning properties and emolliency (when such compositions are included in skin care products) based upon reaction conditions. Thus, by varying the reaction conditions and the type of trialkanolamine and fatty acid used, the compositions according to the present invention may be varied markedly from one composition to another.

Synthesis of Trialkanolamine Fatty Acid Ester

By way of example, the esterification of trialkanolamine with the fatty acid moiety can be carried out in acid catalyzed reactions using well-known catalysts such as well-known methane sulfonic acid, p-toluene sulfonic acid and hypophosphorous acid, among numerous others, at temperatures ranging from about 100° C. to about 250° C., from preferably about 115° C. to 225° C., generally at ambient pressure. Transesterification of a triglyceride such as castor oil with a trialkanolamine can be conducted at temperatures ranging from 85° C. to 150° C. with a caustic (base) catalyst such as sodium hydroxide, sodium methylate, etc. at ambient pressures. The ratio of fatty acid to the Trialkanolamine may be varied from 1 mole of Trialkanolamine to 3 moles of the fatty acid moiety to 1 mole of Trialkanolamine to 1 mole of fatty acid. By varying the weight ratio of trialkanolamine to fatty acid, one or ordinary skill can produce a mono-, di- or triesterified trialkanolamine The present invention relates to polymeric urethane ester quats which are obtained by taking a trialkanolamine such as triethanolamine and esterifying with fatty acids ranging from $C_2$ through $C_{25}$, preferably $C_{10}$ through $C_{22}$, such group of fatty acids including carboxylic acids such as Behenic, Caproic, Caprylic, Capric, Lauric, Myristic, Palmitic, Stearic, Aracidonic Acid, Linoleic, Oleic, erusic, Linoleic, Linolenic, 2-Ethylhexanoic, Isooctanoic, Pelargonic, Heptanoic, Undecanoic, isoluric, Isomyristic, Isopalmitic, Isostearic and mixtures such as those elicited in Coconut Fatty Acids, Palm Kernal Fatty Acids, Soybean Fatty Acids, Safflower Fatty Acids, etc. In addition to the aforementioned acids, alpha hydroxy acids such as lactic acid and glycolic acid, among numerous others as well as beta-hydroxy acids such as salicylic acid as well a ricinoleic and 12-hydroxystearic acid form the mono, di or triesters of a trialkanolamine. Once the fatty acid ester of a trialkanolamine is completed with an acid number under 2.0, the product is thoroughly dried and purified.

The uniqueness of the present invention relates to the reaction of the ester with a suitable isocyanate such as isophorone diisocyanate such that that a polymeric urethane is produced. Other isocyanates which may be used in the present invention including the following: isophoronediisocyanate, m-phenylene-diisocyanate, p-phenylenediisocyanate, 4,4-butyl-m-phenylene-diisocyanate, 4-methoxy-m-phenylenediisocyanate, 4-phenoxy-m-phenylenediisocyanate, 4-chloro-m-phenyldiisocyanate, toluenediisocyanate, m-xylylenediisocyanate, p-xylylenediisocyanate, 1,4-napthalenediisocyanate, cumene-1,4-diisocyanate, durene-diisocyanate, 1,5-napthylenediisocyanate, 1,8-napthylenediisocyanate, 1,5-tetrahydronapthylenediisocyanate, 2,6-napthylenediisocyanate, 1,5-tetrahydronapthylenediisocyanate; p,p-diphylenediisocyanate; 2,4-diphenylhexane-1,6-diisocyanate; methylenediisocyanate; ethylenediisocyanate; trimethylenediisocyanate, tetramethylenediisocyanate, pentamethylenediisocyanate, hexamethylenediisocyanate, nonamethylenediisocyanate, decamethylene-diisocyanate, 3-chloro-trimethylenediisocyanate and 2,3-dimethyltetramethylenediisocyanate, among numerous others.

The urethane reaction of the present invention may occur at the unreacted hydroxyl groups of the trialkanolamine or may take place at the hydroxyl groups of the fatty acid of the trialkanolamine fatty acid ester. The urethane reactions will occur at a temperature range of approximately 60° C. to approximately 140° C. or higher. The ratio of the diisocyanate to trialkanolamine ester may range from about 1:3 to about 3:1 depending upon the number of hydroxyl groups which occur in the trialkanolamine and fatty acid substituents of the ester as well as the desirability of obtaining compositions which are more chain-extended in character rather than crosslinked. A molar ratio of diisocyanate to trialkanolamine ester ranging from about 1:1 to about 1:2 is preferred, with a ratio of about 1:1 to about 1:1.2 in certain more preferable aspects of the present invention.

The resulting polymeric urethane ester is usually a fairly viscous product with activity of 100%, although the viscosity may be adjusted accordingly by changing the molar ratio of the reactants, the type of trialkalonamine used, the type of fatty acid used and the type of diisocyanate used as well as the molar ratios of each of those components used. The quaternarization is, carried out in a procedure in which the present invention is heated to a temperature of ranging from about room temperature to about 100° C. or more, preferably, about 60° C. to about 70° C. preferably in the absence of a diluent or solvent and the quarternarizing agent such as diethyl sulfate, dimethyl sulfate, benzyl chloride, pyridium chloride, among others as set forth in greater detail herein, is slowly added. Once the quaternarization of the present invention is completed, an inert diluent such as propylene glycol, hexylene glycol or other pharmaceutically or cosmetically acceptable diluent may be added to reduce viscosity of the higher moleculer derivative. Alternatively, and depending upon the molecular weight, crosslink density and viscosity of the polyurethane ester, quaterniziation may occur in the presence of a diluent or solvent in addition to the quaternizing agent in order to provide for efficient reaction conditions. One of ordinary skill will known how to readily adjust the conditions by way of temperature and use of solvent, in order to provide compositions according to the present invention.

Final quaternized compositions according to the present invention have been found to be compatible with the esters (emollients), surfactants, emulsifiers and diluents that are used in skin and hair contacting formulations that find use in the cosmetic, toiletry and personal care industries. In addition, the compositions have a low irritation index and are compatable with the skin.

Compositions according to the present invention may be used as additives for compositions used on or to treat keratinous and epithelial tissue such as hair, nails and skin. By the introduction of surfactactants and conditioners into personal care products, it is possible to introduce effective personal care, toiletry and cosmetic products that will achieve highly desirable characteristics.

Effective amounts of the polymeric urethane compositions of the present invention may also function as sheen enhancing agents, as wet-comb and dry-comb facilitators in formulations such as hair coloring products, shampoos and conditioners in the personal care, toiletry and cosmetic industry, as well as thickeners which exhibit favorable surfactant and conditioning characteristics. The compositions according to the present invention are particularly useful in shampoos and conditioning agents where the combined characteristics, which include an enhanced sheen in addition to increased adherance to keratinous tissue, when applied to hair, produce unexpectedly favorable results. This is especially true given the fact that the compositions according to the present invention are compatible with biological systems and demonstrate a low order of toxicity and irritation.

The present compounds inherently bestow upon a cosmetic formulator the ability to achieve a wide range of desirable end characteristics that may be sought in a given formulation by selecting polymeric urethanes according to the present invention and adding it to a composition to be improved or modified.

The novel polymeric urethane compositions of the present invention bring novel unanticipated properties which can be traced to the presence of the "urethane linkage" within the polymer. This linkage synergistically increases adhesion to hair and skin contacting formulations resulting in the use of less quaternary than those products which are available in the current marketplace. In essence, the "urethane linkage" of the present invention magnifies the effectiveness of the cationic properties of the tertiary amine quat, resulting in more desirable properties, more skin compatability and less skin irritation than prior art compositions. This is an unexpected result.

The compositions according to the present invention exhibit unexpectedly long-lasting conditioning and extended antistatic qualities as a result of the "adhesive" character of the urethane functionality. The present compositions form a unique additive for skin and hair contacting formulations which is non-irritating to the skin and eyes and enhances the life and efficiency of a given cosmetic formulation.

The novel polyurethane compositions according to the present invention instill in skin and hair contacting formulations the following results:

1) Increased sheen in hair conditioners.
2) Increased adhesion to the hair shaft wherein the urethane linkage exhibits a synergistic effect with the quaternarized tertiary amine functionality.
3) The increased adhesion characteristics directly attributable to the "urethane linkages" within the polymers of the present invention extend the effectiveness of a given skin and hair contacting formulation.
4) Immensely better wet and dry combing characteristics are attainable by the introduction of the present compositions.
5) The "urethane linkages" of the present invention and the adhesion they promote to the hair shaft prolongs the effectiveness of the antistatic over and above quaternaries which have been in use.
6) The introduction of the present invention to skin and hair contacting formulations bring a velvetty softness and longer lasting conditioning whic is superior to that which is attainable with prior art compositions.
7) Increased color compatability and conditioning for hair color products.

Compositions according to the present invention may be used to formulate a wide variety of personal care products, including skin and hair contacting formulations in the cosmetic, toiletry and personal care industries that have excellent aesthetics heretofore unachievable.

In general, compositions according to the present invention are included in end-use formulations (personal care products) in amounts ranging from about 0.025% to about 50% by weight, more preferably about 0.50% to about 20% by weight, depending upon the end-use.

For example, in shampoos, rinses, conditioners, hair straighteners, hair colorants and permanent wave formulations, the compositions according to the present invention preferably comprise about 0.25% to about 20% by weight, more preferably about 0.25% to about 10% by weight of the final end-use hair-care composition. Other components which may be included in hair-care formulations include, for example, a solvent or diluent such as water and/or alcohol, surfactants, thickeners, coloring agents, preservatives, additional conditioning agents and humectants, among numerous others.

In the case of shave creams and gels, after-shave lotions and shave-conditioning compositions (for example, pre-electric shave formulations), the compositions according to the present invention are included in amounts ranging from about 0.25% to about 15% or more by weight, more preferably about 0.5% to about 10% by weight. Other components which may be included in these end-use compositions include, for example, water, and at least one or more of emollients, humectants and emulsifiers and optionally, other conditioning agents, medicaments, fragrances and preservatives.

In the case of skin lotions and creams, the present compositions are included in amounts ranging from about 0.25% to about 25% by weight, more preferably, about 0.5 to about 10% by weight. Additional components which may be employed in these compositions include, for example, water, emollients and emulsifiers and optionally, other conditioning agents medicaments, fragrances and preservatives.

In the case of sunscreens and skin-protective compositions, the present compositions are included in amounts ranging from about 0.25% to about 20% or more by weight, preferably about 0.5% to about 7.5% by weight of the final formulations. Additional components which may be employed in these compositions may include, for example, a UV absorbing composition such as para-amino benzoic acid (PABA) or a related UV absorber or a pigment such as $TiO_2$, water or oil, and optional components including, for example, one or more of an oil, water, suspending agents, other conditioning agents and emollients, among others.

In the case of bar and liquid soaps, compositions according to the present invention are included in amounts ranging from about 0.25% to about 20% by weight or more, preferably about 0.5% to about 10% by weight. Additional components which may be included in bar and liquid soaps include water and surfactants and optionally, bacteriacides, fragrances and colorants, among others.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Example 1

Polyurethane Triethanolamine/Ricinoleic Acid Ester Diethyl Sulfate Quat

To one mole of triethanolamine, 99% purity, is added two moles of ricinoleic acid in a three-neck 1 liter flask equipped with heat, agitation and nitrogen. To this mixture is added approximately 1 gram of dibutyl tin dilaurate and the mixture in heated to approximately 170 to 225° C. to achieve complete esterification which is measured by the acid number as well as through a determination of the grams of water liberated by the reaction.

The above product is dried and is defined by the following specifications:

| | |
|---|---|
| Appearance | Clear, Dark Amber Viscous Liquid |
| Color, Gardner | 7 |
| Odor | Characteristic |
| Specific Gravity @ 25° C. | 1.4786 |
| Acid Value | 2.0 |
| Alkali Value | 74.5 |

The above diester with an approximate molecular weight of 934 is placed in a three-neck 2 liter flask equipped with heat, agitation and a Nitrogen blanket and dried under 25 inches of vacuum and cooled to approximately 70° C. Approximately 66 grams of Isophorone Diisocyanate is slowly added over a three-hour period. The reaction is monitored on infrared to determine the completion the reaction of the two indicated reactants. The product is defined as follows:

| | |
|---|---|
| Appearance @ 25° C. | Dark Amber Viscous Liquid |
| Color, Gardner | 7+ |
| Odor | Mild |
| Alkali Value | 66.4 |

The above indicated triethanolamine diricinoleate/IPDI copolymer is quaternarized as indicated with diethylsulfate as follows: Approximately 515 grams of the TEA Diricinoleate/IPDI Copolymer is placed into a three-neck 1 liter flask equipped with stirring, heat and a Nitrogen lanket and brought to a temperature of approximately 50° to 75° C. Approximately 92 grams of Diethyl Sulfate is slowly added over a two- to three-hour period and monitored for free amine until the reaction has been completed. The product is defined as follows:

| | |
|---|---|
| Color, Gardner | Clear Amber Viscous Liquid |
| Odor | Characteristic |
| pH of 1.0% Dispersion | 7 |

Propylene Glycol or Hexylene Glycol or similar diluents may be added to the above Polymeric Urethane Ester Quat to enhance ease of handling. Concentrations of such diluents may vary from 10 to 60% of the total weight of the final product.

Example 2

Polyurethane Triethanolamine/Lactic Acid/Erucic Acid Ester Diethyl Sulfate Quat

To one mole of triethanolamine is added one mole of lactic acid (88%) solution and one mole of erucic Acid in a three-neck, one liter flask equipped with agitation, heat and a nitrogen blanket. The reaction is catalyzed by p-toluene sulfonic acid and esterification is completed to an acid number of less than 2.0. Approximately two moles of water are liberated in addition to the 12% of water contained in the lactic acid solution. Reaction occurs at a temperature ranging from 100° C. to approximately 220° C. to effect completion.

One mole of the diester of the above reaction containing two free hydroxyl groups, one being contributed by the lactic acid moiety and the other by the unreacted hydroxyl group of the Triethanolamine entity is thoroughly dried and placed into a three-neck, one liter flask. Drying is effected by evacuating the flask with a pressure of 125 mm. and the introduction of heat of 125° C. To this, triethanolamine lactate/erucic ester is carefully dropped 1.25 moles of Isophorone Diisocyanate at a temperature ranging from 50 to 135° C. The reaction is monitored by infrared to indicate completion of reaction. Reaction will occur over a four-hour period.

The above indicated polymer which comprises triethanolamine lactate/erucic ester/IPDI copolymer is then heated to a temperature of 70° C. and a stoichiometric amount of diethyl sulfate is introduced over a two-hour period at a temperature range of 70 to 80° C. The reaction is monitored by observation of the free amine to indicate completion of reaction

Example 3

Polyurethane Triethanolamine/Salicylicacid/Oleic Acid Ester Diethyl Sulfate Quat To one mole of 99% triethanolamine is added one mole of salicylic acid and one mole of oleic acid in a one liter three-neck flask. To this mixture is added an appropriate amount of methane sulfonic acid and the mixture is heated to ranges of 86 to 165° C. to effect completion of the reaction. A vacuum of 200 mm. may be required to bring the reaction to completion. Once the reaction has been completed under such vacuum that it essentially stops, the mixture is washed and neutralized to bring the acid number down to below 1.0. Once this has been achieved, the product is dried under heat and vacuum.

One mole of the above indicated triethanolamine salicylate/oleate mixture is then placed into a one liter flask and brought to a temperature of 70° C. A tin catalyst such as dibutyl tin dilaurate at a concentration of one gram per mole is added, and then a suitable diisocyanate is slowly dropped into the TEA salicylate/oleate diester. The reaction is monitored with infrared and followed to completion, which should take about four hours.

The polymeric TEA salicylate/oleate IPDI copolymer of which one mole is placed into a one liter flask is introduced a stoichiometric amount of DEA at a temperature of 70 to 80° C. over a three-hour period to effect quaternarization. The reaction is monitored by determination of the free amine to completion.

The present invention introduces the use of the reaction product of diisocyanates such as isophorone diisocyanates and esters of trialkanolamines such as triethanolamine which may range from mono to triesters in the preparation of cosmetic formulations for the purpose of increased adhesion, softness, sheen conditioning; increased efficacy as antistats; increased ease of wet and dry combing; and increased compatibility with existing cosmetic raw materials.

Preferred embodiments of the present invention are presented as the following formulary compositions. Note that in many instances, complex urethane compositions which are not aspects of the present invention are generally available commercially from Alzo, Inc., Sayreville, N.J., USA or can be synthesized pursuant to the teachings available in the art as well as in international patent application nos. WO 00/56285 or WO 99/54027, both of which references are incorporated by reference herein.

FORMULARY A
HAIR CONDITIONER CONCENTRATE

| | INGREDIENT | %, WEIGHT | INCI NAME |
|---|---|---|---|
| A. | Behenylamidopropyl Dimethylamine Behenate | 10.0 | Behenylamidopropyl Dimethylamine Behenate |
| | Triethanolamine Diricinoleate/IPDI Copolymer DES | 3.5 | Triethanolamine Diricinoleate/IPD Copolymer (as prepared above) |
| | Cetyl Alcohol | 2.6 | Cetyl Alcohol |
| | Stearylamidopropyl Dimethylamine | 4.5 | Stearamidopropyl Dimethylamine |
| | Glyceryl Stearate | 1.8 | Glyceryl Stearate |
| | Isosteareth-2-Phosphate | 1.8 | Isosteareth-2-Phosphate |
| | Propylene Glycol | 1.8 | Propylene Glycol |
| B. | Water (Deionized) | 55.8 | Aqua |
| | Fragrance | q.s. | |
| | Color | q.s. | |
| | | 100.0 | |

Procedure:

1. Weigh Propylene Glycol into a beaker and heat to 70–75° C., with stirring. Add the first five ingredients and mix until dissolved while maintaining temperature.
2. Add the Isosteareth-2-Phosphate to the above mixture.
3. With good agitation, add water from Part B to the oil phase.
4. Maintain a temperature of 70–75° C. and mix until uniform.
5. Cool to 40° C. and add Color and Fragrance.

FORMULARY B
SOFT HOLD CONDITIONING MOUSSE

| | INGREDIENT | %, WEIGHT | INCI NAME |
|---|---|---|---|
| A. | Water (Deionized) | 82.85 | Aqua |
| | Triethanolamine Diricinoleate/IPDI Copolymer | 3.00 | Triethanolamine Diricinoleate/IPDI Copolymer |
| B. | Isopropanol | 10.00 | Isopropanol |
| | Aminomethyl Propanol | 0.15 | Aminomethyl Propanol |
| | Butyl Ester of PVM/MA Copolymer | 2.00 | Butyl Ester of PVM/MA Copolymer |
| C. | Dimethicone Copolyol | 3.00 | Dimethicone Copolyol |

Procedure:

1. Add the Triethanolamine Diricinoleate/IPDI Copolymer DES to water and heat to 65° C. to achieve homogeneity.
2. Cool to 40° C.
3. Blend Part B and heat to 65° C. and cool to 40° C.
4. Add Part A to Part B at 40° C.
5. Add Part C with agitation and add Color and Fragrance as required.

FORMULARY C
MOISTURIZING HUMECTANT CREME

| | INGREDIENT | %, WEIGHT | INCI NAME |
|---|---|---|---|
| A. | Water (Deionized) | 66.0 | Aqua |
| | Phenoxyethanol and Methyl Paraben, Ethyl Paraben, Propyl Paraben and Butyl Paraben | 1.0 | Phenoxyethanol and Methyl Paraben, Ethyl Paraben, Propyl Paraben and Butyl Paraben |
| | Diglycerol | 3.5 | Diglycerol |
| | Lactamide MEA | 3.5 | Lactamide MEA |
| | Triethanolamine Diricinoleate/ IPDI Copolymer DES | | Triethanolamine Diricinoleate/ IPDI Copolymer DES |
| B. | Light Mineral Oil | 3.0 | Light Mineral Oil |
| | Benzyl Laurate/Myristate Palmitate | 3.0 | Benzyl Laurate, Myristate Palmitate |
| | Diisopropyl Adipate | 3.0 | Diisopropyl Adipate |
| | Cetyl Alcohol | 5.0 | Cetyl Alcohol |
| | Monoderm N-16 | 5.0 | N/A |
| | Dimethicone (200 C.S,) | 0.2 | Dimethicone |
| | Sorbitan Monostearate | 3.0 | |
| | | 100.0 | |

Procedure:
1. Heat Part A to 65° C. with mixing until clear.
2. Heat B to 70° C.
3. Slowly add Part B to Part A with good agitation and cool slowly.

FORMULARY D
CONDITIONER FOR DAMAGED AND DRY HAIR

| | INGREDIENTS | %, WEIGHT | INCI NAME |
|---|---|---|---|
| A. | Water (Deionized) | 76.40 | Aqua |
| | Propyl Paraben | 0.10 | Propyl Paraben |
| | Methyl Paraben | 0.20 | Methyl Paraben |
| B. | Triethanolamine Diricinoleate/IPDI Copolymer DES | 2.70 | Triethanolamine Diricinoleate/IPDI Copolymer DES |
| | Monoderm N-16 | 2.00 | N/A |
| | Stearylamidopropyl Dimethylamine | 0.50 | Stearamidopropyl-dimethylamine |
| | PEG-150 Tetrastearate Tetrastearate | 1.50 | PEG-150 Pentaryuthritol |
| C. | Behenylamidopropyldi-Behenate methylamine Behenate | 5.00 | Behenylamidopropyl-dimethylamine |
| D. | Polysorbate-80 | 1.80 | Polysorbate-80 |
| | Glycerine | 3.60 | Glycerine |
| E. | PEG-15 Soyamine/IPDI Copolymer | 4.20 | PEG-15 Soyamine/ IPDI Copolymer |
| | | 100.00 | |

Procedure:
1. Dissolve the Parabens in water to 65° C.
2. Melt Part B ingredients and add to Part A with moderate agitation.
3. Mix Part D at 70° C. and add to Parts A,B and stir until uniform.
4. Mix Part D and add to Parts A,B,C and add Part E. Continue to stir at 50° C.

FORMULARY E
CONDITIONING SHAMPOO

| | INGREDIENTS | %, WEIGHT | INCI NAME |
|---|---|---|---|
| A. | Water (Deionized) | 38.32 | Aqua |
| | PEG-15 Soyamine/IPDI Copolymer | 0.75 | PEG-15 Soyamine/ IPDI Copolymer |
| | Methyl Paraben | 0.15 | Methyl Paraben |
| | Propyl Paraben | 0.05 | Propyl Paraben |
| B. | Ammonium Lauryl Sulfate (25%) | 24.00 | Ammonium Lauryl Sulfate |
| | Ammonium Laureth Sulfate (26%) | 14.30 | Ammonium Laureth Sulfate |
| | Cocamidopropyl Betaine (40%) | 11.43 | Cocamidopropyl Betaine |
| C. | Lauramide DEA | 2.00 | Lauramide DEA |
| | Cocamide MEA | 2.50 | Cocamide MEA |
| D. | TEA Diricinoleate/IPDI Copolymer DES | 4.00 | TEA Diricinoleate/ IPDI Copolymer |
| E. | Fragrance | .50 | |
| | Polysorbate-80 | 1.00 | Polysorbate-80 |
| | | 100.00 | |

Procedure:
1. Add the Parabens and PEG-15 Soyamine/IPDI Copolymer to water and stir until uniform.
2. Add Part B slowly to Part A with moderate agitation and bring to 65° C.
3. Melt Part C to 65° C. and add to Part A,B.
4. Combine ingredients of Part D and slowly add to Parts A,B,C at 45° C. with moderate agitation.
5. Add Fragrance to Polysorbate-80 and add to the above blend under 40° C.
6. Continue to stir to room temperature.

FORMULARY F
THERAPEUTIC HUMECTANT CREAM

| | INGREDIENTS | %, WEIGHT | INCI NAME |
|---|---|---|---|
| A. | Water (Deionized) | 65.8 | Aqua |
| | TEA Dierucate/IPDI Copolymer DES | 3.0 | TEA Dierucate/ IPDI Copolymer DES |
| | Phenoxyethanol and Methyl Paraben, Propyl Paraben, Ethyl Paraben and Butyl Paraben | 1.0 | Phenoxyethanol and Methyl Paraben, Propyl Paraben, Ethyl Paraben and Butyl Paraben |
| B. | Monoderm N-16 | 5.0 | N/A |
| | Myristyl Myristate | 5.0 | Myristyl Myristate |
| | Benzyl Laurate, Myristate Palmitate | 3.0 | Benzyl Laurate/ Myristate/Palmitate |
| | Propylene Glycol Monostearate | 2.0 | Propylene Glycol Monostearate |

Procedure:
1. Heat Part A to 65° C. to clarity.
2. Heat Part B 65° C. with mixing.
3. Slowly add Part B to Part A with good mixing and cool slowly.

FORMULARY G
NATURAL SKIN SMOOTHING CREME

| | INGREDIENTS | %, WEIGHT | INCI NAME |
|---|---|---|---|
| A. | Water (Deionized) | 78.6% | Aqua |
| | Phenoxyethanol and Methyl Paraben and Propyl Paraben and Ethyl Paraben and Butyl Paraben | 1.0 | Phenoxyethanol and Methyl Paraben and Propyl Paraben and Ethyl Paraben and Butyl Paraben |
| | TEA Dibehenate/IPDI Co- | 3.0 | TEA Dibehenate/IPDI Copolymer |
| B. | Monoderm N-16 | 5.0 | N/A |
| | Myristyl Myristate | 5.0 | Myristyl Myristate |
| | Benzyl Laurate/Myristate/ | 4.0 | Benzyl Laurate/Myristate/Palmitate |

FORMULARY G
NATURAL SKIN SMOOTHING CREME

| INGREDIENTS | %, WEIGHT | INCI NAME |
|---|---|---|
| Glycereth-7-IPDI Copolymer | 0.4 | Glycereth-7-IPDI Copolymer |
| Dimethiconol/IPDI Copolymer | 1.0 | Dimethiconol/IPDI Copolymer |
| Tocopheryl Acetate | 1.0 | Tocopheryl Acetate |
| Monoderm I-16 | 1.0 | N/A |
| | 100.0 | |

Procedure:
1. Heat Part A to 65° C. to uniformity.
2. Heat Part B to 65° C. to uniformity.
3. Add Part B to Part A with agitation at 65° C. and cool. Fragrance may be added under 40° C.

FORMULARY H
MOISTURIZING CREAM WITH SUNSCREEN

| | INGREDIENTS | %, WEIGHT | INCI NAME |
|---|---|---|---|
| A. | Water (Deionized) | 79.41 | Aqua |
| | TEA Diarichidonate/IPDI Copolymer DES | 2.00 | TEA Diarichidonate/IPDI Copolymer DES |
| | Polyderm PPI-G7-CA | 5.00 | Proposed: Glycereth-7-Diglycerol-PEG-15 Cocamine/IPDI Copolymer |
| | Chloroxylenol | 0.04 | Chloroxylenol |
| B. | Dimethiconol/IPDI Copolymer | 1.00 | Dimethiconol/IPDI Copolymer |
| | Myristyl Myristate | 1.00 | Myristyl Myristate |
| | Cetyl Alcohol | 2.00 | Cetyl Alcohol |
| | Octyl Dimethyl PABA | 5.00 | Octyl Dimethyl PABA |
| | Benzophenone-3 | 3.00 | Benzophenone-3 |
| | Tocopheryl Acetate | 0.05 | Tocopheryl Acetate |
| | Propylene Glycol Monostearate | 1.50 | Propylene Glycol Monostearate |

Procedure:
1. Blend and Peat Part A to 65° C.
2. Blend and heat Part B in a separate container.
3. Add Part B to Part A with agitation at 65° C. and to room temperature.

FORMULARY I
NATURAL MILD CONDITIONING SHAMPOO

| | INGREDIENTS | %, WEIGHT | INCI NAME |
|---|---|---|---|
| A. | Water (Deionized) | 48.5 | Aqua |
| | Di-PEG-2 Soyamine/IPDI Dimer Dilinoleate | 0.5 | Di-PEG-2 Soyamine/IPDI Dimer Dilinoleate |
| B. | Cocoamidopropyl Betaine | 22.0 | Cocoamidopropyl Betaine |
| | PEG-15 Soyamine/IPDI Copolymer | 3.0 | PEG-15 Soyamine/IPDI Copolymer |
| | TEA Dibehenate/IPDI Copolymer DES | 3.0 | TEA Dibehenate/IPDI Copolymer DES |
| | Disodium Oleamido PEG-2 Sulfosuccinate Ether | 10.0 | Disodium Oleamido PEG-2 Sulfusuccinate Ether |
| C. | Sodium Lauryl Sulfate (30%) | 20.0 | Sodium Lauryl Sulfate |
| | Lauramide DEA | 3.0 | Lauramide DEA |
| | Preservative | q.s. | |
| | | 100.0 | |

Procedure:
1. Heat water to 45° C. and with agittion slowly add the PEG-2 Soyamine/IPDI Copolymer Dimer Dilinoleate.
2. Add the Betaine and PEG-15 Soyamine/IPDI Copolymer with slow agitation.
3. Add the Sodium Laureth Sulfate and finally add the Amide. (All of the additions and agitation should be done at 45° C.

FORMULARY J
AFTER SHAVE TONER

| | INGREDIENTS | %, WEIGHT | INCI NAME |
|---|---|---|---|
| A. | Water (Deionized) | 51.00 | Aqua |
| | Carbomer 940 | 0.35 | Carbomer 940 |
| | Triethanolamine, 99% | 0.6 | Triethanolamine |
| B. | Water (Deionized) | 30.35 | Aqua |
| | TEA Triricinoleate/IPDI Copolymer DES | 1.00 | TEA Triricinoleate/IPDI Copolymer DES |
| | Ethanol, SD-40 | 15.00 | Ethanol, SD-40 |

-continued

FORMULARY J
AFTER SHAVE TONER

| | INGREDIENTS | %, WEIGHT | INCI NAME |
|---|---|---|---|
| C. | Dimethiconol-PEG-15 | 2.00 | Dimethiconol-PEG-15 |
| | Soyamine/IPDI Copolymer | 100.00 | Soyamine/IPDI Copolymer |

Procedure:
1. Slowly add Carbomer 940 to water with good agitation and add TEA to make a clear, viscous solution.
2. Add Part B to a separate container and heat to 40° C. and add the Ethanol.
3. Add Part B to Part A.
4. Add Part C to Part A,B.

FORMULARY K
SHOWER GEL

| | INGREDIENTS | %, WEIGHT | INCI NAME |
|---|---|---|---|
| A. | Water (Deionized) | 55.0 | Aqua |
| | Sodium Chloride | 1.0 | Sodium Chloride |
| | Sodium Laureth Sulfate | 35.0 | Sodium Laureth Sulfate |
| | Cocoamidopropyl Betaine | 5.0 | Cocoamidopropyl Betaine |
| | TEA Triricinoleate/IPDI Copolymer DES | 2.0 | TEA Triricinoleate/IPDI Copolymer DES |
| | Lauramide DEA | 2.0 | Lauramide DEA |
| | | 100.0 | |

Procedure:
1. Add Salt, TEA Triricinoleate/IPDI Copolymer DES and Cocoamidopropyl Betaine to water and heat to clarity at 60° C.
2. Add the Sodium Laureth Sulfate and Lauramide DEA and continue to mix to cooling.

FORMULARY L
AFTER SHAVE LOTION

| | INGREDIENTS | %, WEIGHT | INCI NAME |
|---|---|---|---|
| A. | Water (Deionized) | 59.61 | Aqua |
| | Disodium EDTA | 0.02 | Disodium EDTA |
| | SD Alcohol-40 | 15.00 | SD Alcohol-40 |
| | Phenoxyethanol and Methyl Paraben and Ethyl Paraben Propyl Paraben and Butyl Paraben | 0.06 | Phenoxyethanol and Methyl Paraben and Ethyl and Propyl Paraben and Butyl Paraben |
| | Polyderm PPI-G7-CA | 3.00 | Proposed: Glycereth-7-Diglycerol-PEG-15 Cocamine/IPDI Copolymer |
| B. | Diisopropyl Adipate | 5.00 | Diisopropyl Adipate |
| | TEA Triricinoleate/IPDI Copolymer DES | 2.00 | TEA Triricinoleate/IPDI Copolymer DES |
| | Octyl Hydroxystearate | 6.00 | Octyl Hydroxystearate |
| | Tocopheryl Acetate | 0.20 | Tocopheryl Acetate |
| | Glyceryl Tricaprylate/ | 0.80 | Glyceryl Tricaprylate/Tricaprate |
| | Dimethyl Lauryl Amine Oleate | 2.00 | Dimethyl Lauryl Amine Oleate |
| | Polysorbate-85 | 1.50 | Polysorbate-85 |
| C. | Fragrance | 1.00 | |
| | | 100.00 | |

Procedure:
1. Combine Part A at room temperature with good agitation.
2. Combine Part B and agitate for 15 to 20 minutes.
3. Add Part B to Part A slowly and continue to agitate for 15 minutes.
4. Add Part C to Parts A,B.

FORMULARY M
SHOWER GEL SHAMPOO

| | INGREDIENTS | %, WEIGHT | INCI NAME |
|---|---|---|---|
| A. | Sodium Lauryl Sulfate (30%) | 20.0 | Sodium Lauryl Sulfate |
| | Alpha Olefin Sulfonate (40%) | 10.0 | $C_{14}$–$C_{16}$ Sulfonate |
| | Disodium Oleamido PEG-2 Sulfosuccinate | 10.0 | Disodium Oleamido PEG-2 Sulfosuccinate |

-continued

FORMULARY M
SHOWER GEL SHAMPOO

| INGREDIENTS | %, WEIGHT | INCI NAME |
| --- | --- | --- |
| Cocoamidopropyl Betaine (45%) | 10.0 | Cocoamidopropyl Betaine |
| Cocoamidopropylamine Oxide | 3.0 | Cocoamidopropylamine Oxide |
| Triethanolamine Diricinoleate/ IPDI DES | 1.0 | Triethanolmine Diricinoleate/IPDI Copolymer DES |
| Color, Fragrance, Preservative Water (Deionized) | q.s. to 100.0 | |

Procedure:
1. Heat water to 50° C. With stirring, add TEA Diricinoleate/ IPDI Copolymer DES.
2. Add Cocoamidopropyl Betaine and then slowly add the Amine Oxide and Sulfosuccinate.
3. Slowly add the Alpha Olefin Sulfonate.
4. Increase stirring and add the Sodium Lauryl Sulfate and cool.

Toxicity Studies

Irritation Studies

Eye Irritation Study of Polyurethane Triethanolamine/Ricinoleic Acid Diethyl Sulfate Quat (Example 1)

Six normal healthy New Zealand white rabbits were used for this study. On the day of the study prior to testing, each animal had their eyes examined for irritation or corneal damage; any animal exhibiting abnormalities was excluded from testing.

Each animal had 0.5 ml of the diluted test material (Polyurethane triethanolamine/ricinoleic acid diethyl sulfate quat in 1.0% WFI1) instilled into the conjuctival sac of the test eye. The contralateral untreated eye served as a control for that animal.

The treated and untreated eyes were examined and graded at 1, 24, 48 and 72 hours post instillation. Only the 24, 48 and 72 hour observation scores are used to determine the irritation potential.

A test is interpreted as positive in this test if four or more animals exhibit a positive response on the cornea, iris or conjunctiva. A test is interpreted as negative if one or less animals exhibit a positive response of the cornea, iris or conjuctiva. A test is considered inconclusive if two or three animals exhibit a positive response on the cornea, iris or conjunctiva. The test may be repeated with a different group of six animals and is positive if three or more animals exhibit a positive response.

Polyurethane triethanolamine/ricinoleic acid diethyl sulfate quat in 1% WFI produced very slight erythema in four of six animals tested. Additionally, three rabbits had above normal discharge. At 24 hours, three rabbits showed very slight erythema with some vessels injected. At both the 48 hour and 72 hour observation timepoints, all rabbits appeared unremarkable. Consequently, the material was not considered a primary eye irritant as defined by the Federal Hazardous Substances Act, 16 CFR 1500.3 (c) (4).

Dermal Irritation Study of Polyurethane Triethanolamine/ Ricinoleic Acid Diethyl Sulfate Quat The test was designed to identify substances which are primary irritants to rabbit skin.

Method of Assay

Six New Zealand white rabbits were used in this test. Animals were acclimated for at least four days prior to initiation of the study. They were housed in clean cages, in a temperature controlled environment with a twelve hour light/dark cycle. Diet consisted of a growth and maintenance ration obtained from a commercial producer (Purina Lab Diet for rabbits), and water, ad libitum. Each animal was identified by an individual tatoo number on one ear, as well as a corresponding cage number and history card.

About 4 and ½ hours before test initiation, the animals were prepared for testing by close-clipping the skin of the mid-dorsal area of the trunk, between the scapulae and the pelvis, using a small animal clipper.

Two test sites, each 2.5 cm square, were chosen on opposite sides of the vertebral column. One site was maintained intact while the other site was abraded with a sterile hypodermic needle. The abrasions are epidermal incisions, sufficiently deep to penetrate the stratum corneum, but not so deep as to destroy the integrity of the derma.

A single application of 0.5 ml. of test material (1% Polyurethane triethanolamine/ricinoleic acid diethyl sulfate quat in WFI) was applied to each test site and each site was then covered with a one-inch square gauze patch.

After both test sites were treated, the entire trunk of each animal was encased in an impermeable occlusive wrapping held in place with Elastikon tape. This aided in maintaining the test material and patches in position and prevents the evaporation of any possible volatile components in the material.

The wrapping and test article were removed 24 hours following application; any remaining test material was gently wiped from the skin using lukewarm water. Each test site was individiually examined and scored at twenty-four and seventy-two hours post dosing for erythema and edema using the Draize skin scoring scale. The presence of effects not listed in the scoring scale was also noted.

Interpretation of Assay

Following the seventy-two hour reading, the scores for twenty-four and seventy-two hour gradings were averaged to determine the primary irritation index. A score of 5.0 or more indicates a primary dermal irritant.

Summary

The test material, under occluded test conditions, produced very slight, barely perceptible erythema in one rabbit on the abraded skin at the 24 hour observation. All other rabbits were unremarkable at the 24 h our observation. All six rabbits were unremarkable at the 72 hour observation. The primary irritation score was 0.04. This is consistent with being classified as a non-skin irritant.

Acute Oral Toxicity

This test was conducted to determine the degree of toxicity that the test substance may produce when administered orally to white rates in a total oral dose of 5 grains per kilogram of body weight.

During the acclimation and testing period, each animal was housed and maintained according to the "Guide for the Care and Use of Laboratory Animals" (NIH 86-23). All animals were identified by the ear hole-notch method and had cage cards which provided the individual animal and project numbers. The animals were single housed in suspended wire cages and fed Purina rodent chow and city water, ad libitum. All animals were acclimated at least 7 days prior to testing.

Procedure

Animals were fasted overnight, approximately 18 hours prior to dosing. The test material, Polyurethane triethanolamine/ricinoleic acid diethyl sulfate quat, was administered orally as a single dose via syringe and suitable intubation tube. The total dose of 5 g/kg of body weight was based on the concentration/density of the test material which was 1.06110 g/ml. The animals were examined for signs of toxicity immediately after dosing, four hours later and then daily for a maximum of 14 days. All observations were recorded on either the daily health observation, body weight or necropsy raw data sheets. Observations involved the following: behavioral abnormalities; gross necropsy; body weight changes; mortality; any other toxicological effects.

Summary

The test material was administered to a group of 10 white rates (5 males, 5 females) to evaluate its toxic characteristics in accordance with Federal requirements as listed in 16 CFR 1500.3(c)(2)(i). A total oral dosage (5 gm/kg body weight) was given and the animals were observed for 14 days thereafter. Any and all behavioral/clinical abnormalities including mortalitites were recorded. All animals appeared unremarkable throughout the 14 day study period.

No mortalities occured during the observation period. Animals were sacrificed at the conclusion of the study. There were no gross abnormalities observed which were attributable to the teset material in any of the animals at necropsy.

Conclusion

The submitted material, when administered as a single oral dosage leve of 5 g/kg body weight, did not produce compound related mortality in half or more of the animals; therefore, the $LD_{50}$ is greater than 5 g/kg and the test material is not considered to be orally toxic according to definitions listed in 16 CFR 1500.3(c)(2)(i).

It is to be understood by those skilled in the art that the foregoing description and examples are merely illustrative of the present invention, and should in no way be intrepreted as limiting the scope of the present invention. Variations of the detail presented herein may be made without departing from the spirit and scope of the present invention as defined by the following claims.

What is claimed is:

1. A composition produced by the method of:
   a. producing a trialkanolamine fatty acid ester comprising reacting a trialkanolamine according to the general structure:

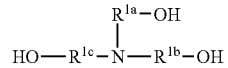

wherein each of $R^{1a}$ $R^{1b}$ and $R^{1c}$ is the same or different and is a $C_2$ to $C_{12}$ saturated or unsaturated, linear, branch-chained, cyclic or aromatic hydrocarbon group which is either unsubstituted or substituted with a pendant hydroxyl group, with a $C_2$ to $C_{25}$ acid optionally having at least one free hydroxyl group or a triglyceride comprising $C_{10}$ to $C_{25}$ fatty acids optionally having at least one free hydroxyl group under conditions effective to produce a trialkanolamine mono-, di- or trifatty acid ester and then reacting said trialkanolamine fatty acid ester with a $C_4$ to $C_{24}$ diisocyanate to produce a polyurethane trialkanolamine fatty acid ester.

2. The composition according to claim 1 having the chemical formula I:

Formula I

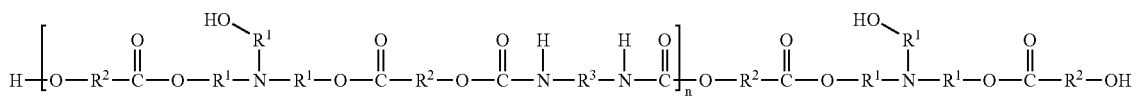

wherein $R^1$ is a $C_2$ to $C_{12}$ saturated or unsaturated, linear, branch-chained, cyclic or aromatic hydrocarbon group which is unsubstituted;

$R^2$ is a $C_1$ to $C_{24}$ saturated or unsaturated, linear, branch-chained, cyclic or aromatic hydrocarbon group wherein said hydrocarbon group may be a phenyl or benzyl group or substituted phenyl or benzyl group, an alkylphenyl, alkylbenzyl or a substituted alkylphenyl or alkylbenzyl group;

$R^3$ is a $C_2$ through $C_{22}$ linear, cyclic or branch-chained saturated or unsaturated hydrocarbon group which is substituted or unsubstituted, an aromatic group, including a phenyl or benzyl group or substituted phenyl or benzyl group, an alkylphenyl, alkylbenzyl or substituted alkylphenyl or alkylbenzyl group; and n is an integer from 2 to 1000.

3. The composition according to claim 1 wherein said fatty acid is selected from the group consisting of behenic, caproic, caprylic, capric, lauric, myristic, palmitic, stearic, arachidonic acid, linoleic, oleic, linoleic, linolenic, 2-ethylhexoic, isooctanoic, pelargonic, heptanoic, undecanoic, isoluric, isomyristic, isopalmitic, isostearic, coconut fatty acids, palm kernal fatty acids, soybean fatty acids, safflower fatty acids, castor oil fatty acids, lactic acid, glycolic acid, glycolic acid, alpha hydroxy butyric acid, alpha hydroxy pentanoic acid, alpha hydroxy hexanoic acid, alpha hydroxy heptanoic acid, alpha hydroxy octanoic acid, alpha hydroxy nonanoic acid, alpha hydroxy decanoic acid, alpha hydroxy dodecanoic acid, salicylic acid, ricinoleic acid, 12-hydroxystearic acid, erucic acid, oleic acid, behenic acid and mixtures, thereof.

4. The composition according to claim 1 wherein said fatty acid is selected from the group consisting of ricinoleic acid, oleic acid, erucic acid lactic acid, salicylic acid and mixtures, thereof.

5. The composition according to claim 1 which is further quaternized with a quaternizing agent.

6. The composition according to claim 1 wherein said diisocyanate is selected from the group consisting of isophoronediisocyanate, m-phenylene-diisocyanate, p-phenylenediisocyanate, 4,4-butyl-m-phenylene-diisocyanate, 4-methoxy-m-phenylenediisocyanate, 4-phenoxy-m-phenylenediisocyanate, 4-chloro-m-phenyldiisocyanate, toluenediisocyanate, m-xylylenediisocyanate, p-xylylenediisocyanate, 1,4-napthalenediisocyanate, cumene-1,4-diisocyanate, durene-diisocyanate, 1,5-napthylenediisocyanate, 1,8-napthylenediisocyanate, 1,5-tetrahydronaphthylenediisocyanate, 2,6-naphthylenediisocyanate, 1,5-tetrahydronaphthylenediisocyanate; p,p-diphylenediisocyanate; 2,4-diphenylhexane-1,6-diisocyanate; methylenediisocyanate; ethylenediisocyanate; trimethylenediisocyanate, tetramethylenediisocyanate, pentamethylenediisocyanate, hexamethylenediisocyanate, nonamethylenediisocyanate, decamethylene-diisocyanate, 3-chloro-trimethylenediisocyanate and 2,3-dimethyltetramethylenediisocyanate and mixtures thereof.

7. The composition according to claim 1 wherein said diisocyanate is isophorone diisocyanate.

8. The composition according to claim 5 wherein said quaternizing agent is selected from the group consisting of dimethyl sulfate, diethyl sulfate, methyl bromide, benzyl chloride, ethyl benzyl chloride, methyl benzyl chloride, dichloroethyl ether, epichlorohydrin, ethylene chlorohydrin, methyl chloride, pyridinium chloride and allyl chloride.

9. The composition according to claim 1 wherein said triglyceride is selected from the group consisting of castor oil, palm kernel oil, soybean oil, safflower oil and rape seed oil.

10. A polymeric composition produced by the process of:
a. reacting a trialkanolamine according to the general structure:

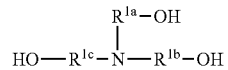

wherein each of $R^{1a}$ $R^{1b}$ and $R^{1c}$ is the same or different and is a $C_2$ to $C_{12}$ saturated or unsaturated, linear, branch-chained, cyclic or aromatic hydrocarbon group which is either unsubstituted or substituted with a pendant hydroxyl group, with a $C_2$ to $C_{25}$ acid optionally having at least one free hydroxyl group or a triglyceride comprising $C_{10}$ to $C_{25}$ fatty acids optionally having at least one free hydroxyl group under conditions effective to produce a trialkanolamine mono-, di- or trifatty acid ester;

b. reacting said trialkanolamine fatty acid ester according to step a with a $C_4$ to $C_{24}$ diisocyanate under conditions effective to cause polymerization of said ester with said diisocyanate to produce a polyurethane trialkanolamine fatty acid ester; and c. reacting said polyurethane trialkanolamine fatty acid ester according to step b with a quaternizing agent to produce a polyurethane trialkanolamine fatty acid ester quat.

11. The composition according to claim 10 wherein said fatty acid is selected from the group consisting of behenic, caproic, caprylic, capric, lauric, myristic, palmitic, stearic, arachidonic acid, linoleic, oleic, linoleic, linolenic, 2-ethylhexoic, isooctanoic, pelargonic, heptanoic, undecanoic, isoluric, isomyristic, isopalmitic, isostearic, coconut fatty acids, palm kernal fatty acids, soybean fatty acids, safflower fatty acids, castor oil fatty acids, lactic acid, glycolic acid, glycolic acid, alpha hydroxy butyric acid, alpha hydroxy pentanoic acid, alpha hydroxy hexanoic acid, alpha hydroxy heptanoic acid, alpha hydroxy octanoic acid, alpha hydroxy nonanoic acid, alpha hydroxy decanoic acid, alpha hydroxy dodecanoic acid, salicylic acid, ricinoleic acid, 12-hydroxystearic acid, erucic acid, oleic acid, behenic acid and mixtures, thereof.

12. The composition according to claim 10 wherein said fatty acid is selected from the group consisting of ricinoleic acid, oleic acid, erucic acid lactic acid, salicylic acid and mixtures, thereof.

13. The composition according to claim 10 wherein said diisocyanate is selected from the group consisting of isophoronediisocyanate, m-phenylene-diisocyanate, p-phenylenediisocyanate, 4,4-butyl-m-phenylene-diisocyanate, 4-methoxy-m-phenylenediisocyanate, 4-phenoxy-m-phenylenediisocyanate, 4-chloro-m-phenyldiisocyanate, toluenediisocyanate, m-xylylenediisocyanate, p-xylylenediisocyanate, 1,4-napthalenediisocyanate, cumene-1,4-diisocyanate, durene-diisocyanate, 1,5-napthylenediisocyanate, 1,8-napthylenediisocyanate, 1,5-tetrahydronaphthylenediisocyanate, 2,6-naphthylenediisocyanate, 1,5-tetrahydronaphthylenediisocyanate; p,p-diphylenediisocyanate; 2,4-diphenylhexane-1,6-diisocyanate; methylenediisocyanate; ethylenediisocyanate; trimethylenediisocyanate, tetramethylenediisocyanate, pentamethylenediisocyanate, hexamethylenediisocyanate, nonamethylenediisocyanate, decamethylene-diisocyanate, 3-chloro-trimethylenediisocyanate and 2,3-dimethyltetramethylenediisocyanate and mixtures thereof.

14. The composition according to claim 10 wherein said diisocyanate is isophorone diisocyanate.

15. The composition according to claim 10 wherein said quaternizing agent is selected from the group consisting of dimethyl sulfate, diethyl sulfate, methyl bromide, benzyl chloride, ethyl benzyl chloride, methyl benzyl chloride, dichloroethyl ether, epichlorohydrin, ethylene chlorohydrin, methyl chloride, pyridinium chloride and allyl chloride.

16. The composition according to claim 10 wherein said triglyceride is selected from the group consisting of castor oil, coconut oil, palm kernel oil, soybean oil, safflower oil and rape seed oil.

17. A composition having the chemical formula I:

Formula I

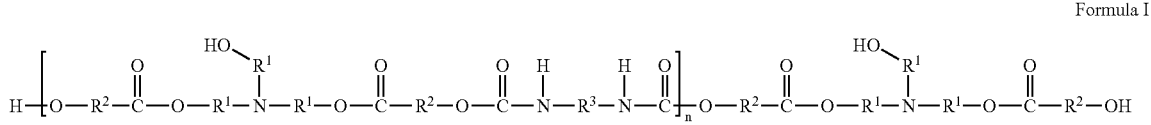

wherein $R^1$ is a $C_2$ to $C_{12}$ saturated or unsaturated, linear, branch-chained, cyclic or aromatic hydrocarbon group which is either unsubstituted or substituted with a pendant hydroxyl group;

$R^2$ is a $C_1$ to $C_{24}$ saturated or unsaturated, linear, branch-chained, cyclic or aromatic hydrocarbon group wherein said hydrocarbon group may be a phenyl or benzyl group or substituted phenyl or benzyl group, an alkylphenyl, alkylbenzyl or a substituted alkylphenyl or alkylbenzyl group;

$R^3$ is a $C_2$ through $C_{22}$ linear, cyclic or branch-chained saturated or unsaturated hydrocarbon group which is substituted or unsubstituted, an aromatic group, including a phenyl or benzyl group or substituted phenyl or benzyl group, an alkylphenyl, alkylbenzyl or substituted alkylphenyl or alkylbenzyl group; and n is an integer from 2 to 1,000.

18. The composition according to claim 17 wherein $R^1$ is an unsubstituted hydrocarbon group.

19. The composition according to claim 17 wherein $R^2$ is a $C_9$ to $C_{24}$ hydrocarbon group.

20. The composition according to claim 17 wherein $R^3$ is a $C_6$ to $C_{12}$ hydrocarbon group.

21. The composition according to claim 17 wherein $R^3$ is an isophorone group.

22. A composition having the chemical formula II:

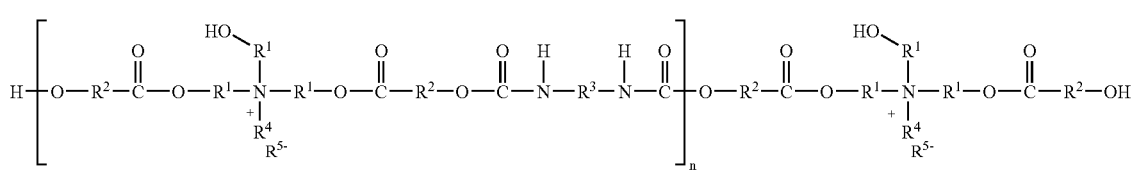

Formula II wherein $R^1$ is a $C_2$ to $C_{12}$ saturated or unsaturated, linear, branch-chained, cyclic or aromatic hydrocarbon group which is either unsubstituted or substituted with a pendant hydroxyl group, but is preferably unsubstituted;

$R^2$ is a $C_1$ to $C_{24}$ saturated or unsaturated, linear, branch-chained, cyclic or aromatic hydrocarbon group wherein said hydrocarbon group may be a phenyl or benzyl group or substituted phenyl or benzyl group, an alkylphenyl, alkylbenzyl or a substituted alkylphenyl or alkylbenzyl group;

$R^3$ is a $C_2$ through $C_{22}$ (preferably, $C_6$ through $C_{12}$) linear, cyclic or branch-chained saturated or unsaturated hydrocarbon group which is substituted or unsubstituted, an aromatic group, including a phenyl or benzyl group or substituted phenyl or benzyl group, an alkylphenyl, alkylbenzyl or substituted alkylphenyl or alkylbenzyl group;

$R^4$ is a quaternizing group;

$R^5$ is a counterion to the quaternizing group; and n is an integer from about 2 to 1,000.

23. The composition according to claim 22 wherein $R^4$ is selected from the group consisting of methyl, ethyl, propyl, benzyl, phenyl, alkyl benzyl, ethyl, propyl, benzyl, phenyl, alkyl benzyl, allyl methyl and allyl.

24. The composition according to claim 22 wherein $R^5$ is selected from the group consisting of anionic chloride, bromide, iodide, fluoride, carboxylate, mono- or dianionic sulfate and mono-, di- and tri-anionic phosphate.

25. The composition according to claim 22 wherein $R^5$ is selected from the group consisting of anionic chloride, methyl sulfate and ethyl sulfate.

26. The composition according to claim 22 wherein $R^1$ is an unsubstituted hydrocarbon group.

27. The composition according to claim 22 wherein $R^2$ is a $C_9$ to $C_{24}$ hydrocarbon group.

28. The composition according to claim 22 wherein $R^3$ is a $C_6$ to $C_{12}$ hydrocarbon group.

29. The composition according to claim 22 wherein $R^3$ is an isophorone group.

30. A method of making a polyurethane composition for use in personal products comprising:

a. reacting a trialkanolamine according to the general structure:

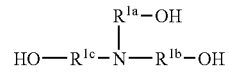

wherein each of $R^{1a}$ $R^{1b}$ and $R^{1c}$ is the same or different and is a $C_2$ to $C_{12}$ saturated or unsaturated, linear, branch-chained, cyclic or aromatic hydrocarbon group which is either unsubstituted or substituted with a pendant hydroxyl group, with a $C_2$ to $C_{25}$ acid having at least one free hydroxyl group or a triglyceride comprising $C_{10}$ to $C_{25}$ fatty acids having at least one free hydroxyl group under conditions effective to produce a trialkanolamine mono-, di- or trifatty acid ester;

b. reacting said trialkanolamine fatty acid ester according to step a with a $C_4$ to $C_{24}$ diisocyanate under conditions effective to cause polymerization of said ester with said diisocyanate to produce a polyurethane trialkanolamine fatty acid ester; and c. reacting said polyurethane trialkanolamine fatty acid ester according to step b with a quaternizing agent to produce a polyurethane trialkanolamine fatty acid ester quat.

31. The method according to claim 30 wherein said trialkanolamine fatty acid ester is a trialkanolaminedifatty acid ester.

* * * * *